(12) United States Patent
Hardart et al.

(10) Patent No.: US 10,687,977 B1
(45) Date of Patent: Jun. 23, 2020

(54) DEVICE AND METHOD TO OPTIMIZE THE FORM AND FUNCTION OF A PESSARY

(71) Applicant: Anne Hardart, New York, NY (US)

(72) Inventors: Anne Hardart, New York, NY (US); John Crombie, East Hanover, NJ (US)

(*) Notice: Subject to any disclaimer, the term of this patent is extended or adjusted under 35 U.S.C. 154(b) by 821 days.

(21) Appl. No.: 15/072,119

(22) Filed: Mar. 16, 2016

Related U.S. Application Data

(60) Provisional application No. 62/126,744, filed on Mar. 2, 2015.

(51) Int. Cl.
*A61F 6/08* (2006.01)
*A61B 5/00* (2006.01)

(52) U.S. Cl.
CPC .............. *A61F 6/08* (2013.01); *A61B 5/6853* (2013.01)

(58) Field of Classification Search
CPC ........ A61F 6/08; A61F 2/005; A61F 13/2082; A61F 2/0027; A61F 2/82; A61F 2/958; A61F 6/00; A61B 5/1076; A61B 5/6853; A61B 17/42; A61M 25/10; A61M 25/1002; A61M 25/0009; A61M 25/1011
USPC ........... 128/834, 836; 600/29, 591; 606/193; 604/96.01
See application file for complete search history.

(56) References Cited

U.S. PATENT DOCUMENTS

| | | | |
|---|---|---|---|
| 3,970,090 A * | 7/1976 | Loiacono | A61M 25/04 604/104 |
| 5,406,961 A | 4/1995 | Artal | |
| 5,653,690 A * | 8/1997 | Booth | A61M 25/04 604/103.07 |
| 5,771,899 A | 6/1998 | Martelly | |
| 6,470,219 B1 | 10/2002 | Novasys | |
| 8,728,013 B2 | 5/2014 | Perle | |
| 2005/0016545 A1 | 1/2005 | Nissenkorn | |
| 2005/0049509 A1 * | 3/2005 | Mansour | A61B 5/1076 600/476 |
| 2007/0016391 A1 | 1/2007 | Minoguchi | |
| 2007/0027667 A1 | 2/2007 | Osborn | |
| 2009/0296980 A1 | 12/2009 | Yi | |
| 2010/0168784 A1 * | 7/2010 | Pustilnik | A61B 17/42 606/193 |
| 2013/0192606 A1 | 8/2013 | Ziv | |
| 2013/0237771 A1 | 9/2013 | Runkewitz | |
| 2013/0296837 A1 * | 11/2013 | Burnett | A61B 18/02 606/21 |
| 2014/0276234 A1 * | 9/2014 | Hines | A61B 5/1076 600/591 |

* cited by examiner

*Primary Examiner* — Anna K Kinsaul
*Assistant Examiner* — Caitlin A Carreiro
(74) *Attorney, Agent, or Firm* — Chan Hubbard PLLC; Keala Chan

(57) ABSTRACT

A device for modeling a pessary is disclosed. A matrix of individually expandable balloons are mounted around a shaft, which holds fill lines for each balloon. The balloons are expandable with fluid to a desired volume and/or pressure, according to comfort and fit determined by real-time patient feedback. Because the volumes and the positions of the balloons are known, a calculation of the dimensions of the vaginal canal can be made, so that the matrix of expandable balloons models the vaginal canal.

20 Claims, 10 Drawing Sheets

DEVICE AND METHOD TO OPTIMIZE THE FORM AND FUNCTION OF A PESSARY

FIELD OF THE INVENTION

The invention lies in the field of pessaries and other vaginal devices.

BACKGROUND

The present invention is a device and method to design a pessary. Typical pessaries today are vaginal devices, usually made of silicone, and often in the shape of a ring or disk. They are often used as a treatment for pelvic organ prolapse and for stress urinary incontinence, conditions that affect at least 25% of the female population. Pessaries are the nonsurgical standard of care for treatment of pelvic organ prolapse and are a common treatment option for stress incontinence. While less common, pessaries may also have additional therapeutic and/or diagnostic functions, such as sensors to measure physiologic parameters including temperature or indicators of ovulation or pre-term labor, modified shape for preventing preterm delivery, or electronic capabilities to stimulate the vaginal wall. The shape, structure and functions of a pessary have remained largely unchanged over time. Problems associated with pessaries are often caused by suboptimal fit resulting in inadequate symptom control, discomfort, bleeding, discharge, vaginal erosions, and difficult removal. Surgery may be the only alternative for a patient who cannot be properly fitted with a pessary.

The previous solutions for determining pessary fit were meant to be as efficient and non-invasive as possible. The most commonly used solution for determining pessary fit was an in-office fitting of fixed sample sizes, in which a clinician fitted sample sizes into the patient and determined the best fit in real time by observation and patient feedback. Another previous solution was the inflatable pessary that could be inserted by the patient and inflated to optimal size. The inflatable pessary proved to be uncomfortable, was often of suboptimal fit, and required more insertion and removal than was desirable to patients.

SUMMARY

The invention is a device that models the interior of the vagina using a matrix of balloons, each balloon on the matrix being individually inflatable, its fill volume controllable by the clinician such that a desired form and fit for the patient can be achieved. The fill volume data and the position of each balloon in the matrix determines a pessary—or other vaginal device—model, which can be further manipulated using computer-aided design. This model facilitates the speedy production and duplication of a personalized or customized pessary. Furthermore, insofar as the device gives the clinician the ability to collect data adaptably and with patient feedback, the invention can also serve as a research tool, a clinical tool and/or a diagnostic tool. New pessary designs can be created, and previously created measurements evaluated.

The device comprises a balloon matrix arranged around a hollow shaft, which can hold fill lines for the individual balloons, such that the individual balloons are separately inflatable with a fluid. The balloons are spherical and inflate uniformly, their positions held in place by a spherical segment support structure in which the balloon nests. Each balloon is delivered fluid by a fill line and a fluid source, in the preferred embodiment the fluid source being a system comprising a solenoid valve manifold directing fluid from a reservoir to the user-selected balloon via the fill line. A flowmeter measures the fill volume of the balloon. Said volume data determines the diameter of the sphere by the mathematical formula $V=(4/3)\pi R^3$. Because the balloon positions are fixed in a matrix, this matrix of balloons models the interior of the vagina simply using the volume data corresponding to each balloon. Additional data may be collected for each balloon, and in particular, pressure data can be collected and monitored to further assist the clinician while inflating the device. For instance, application of pressure against the bladder neck can be useful data for diagnoses and treatments for urinary incontinence. Furthermore, where gas is used for inflation pressure in conjunction with temperature within the vaginal canal can be used to approximate or determine the volume of each balloon. By inflating and deflating individual balloons to suitable volume/pressure, in conjunction with real-time patient feedback, the clinician can determine desired comfort and fit, as well as record data and changes in shape and pressure.

DETAILED DESCRIPTION

Figure 1A:
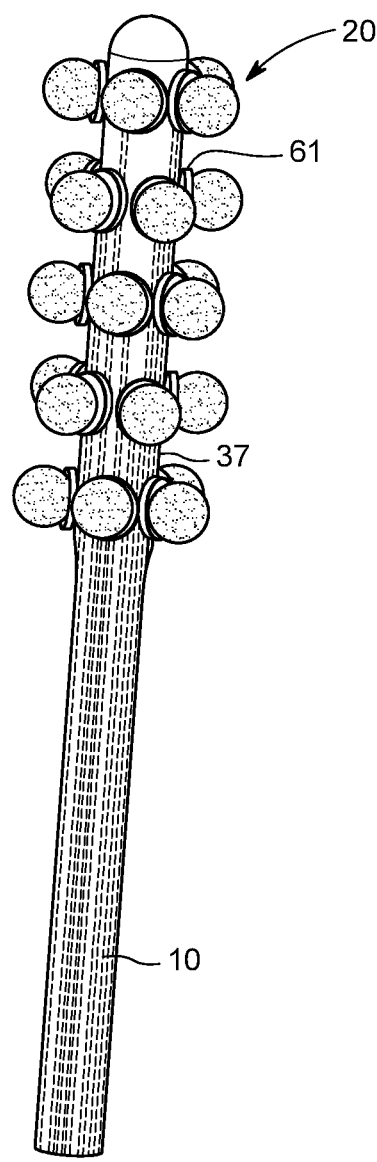
FIG. 1A shows a balloon matrix before inflation.
Figure 1B:
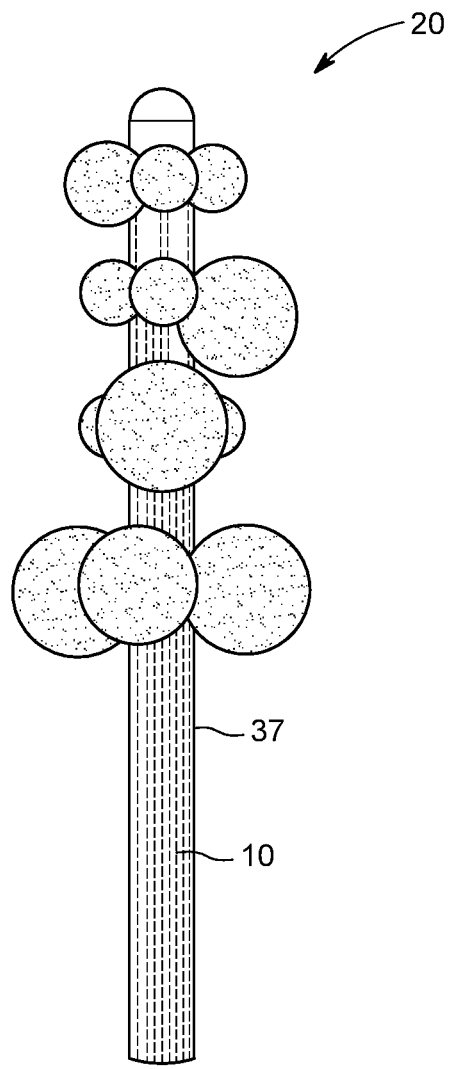
FIG. 1B shows a balloon matrix after inflation customized to a patient.

FIGS. 1A and 1B give a first overview of the invention, in which a plurality of expandable balloons 20, removably attached to a shaft 37, which is insertable into the vagina, collectively model the interior structure of the vagina. Each expandable balloon—such as balloons 21, 22, 23, 24, 25 and 26 in FIG. 2—is connected to a fill line, such as fill lines 1, 2, 3, 4, 5 and 6, whereby each expandable balloon is inflatable and deflatable via a corresponding fill line. Each expandable balloon is spherical and expands uniformly, and its position on the shaft is known. With the expansion of a single balloon, a desired pressure against the corresponding part of the vaginal wall may be determined. This desired pressure can be determined by any method preferred by the clinician, for instance, by ascertaining what pressure exerted by the balloon volumes adequately support the vaginal walls without causing discomfort. Subjective input from the patient during the fitting assists the clinician in determining optimal pressure/volume of the balloons. Collectively, the expansion of the entire array of balloons 20 may determine the dimensions of a customized pessary.

The insertable shaft 37 houses the corresponding fill lines 10 and supports the expandable balloons for insertion into the vagina. The distal part of the shaft supports the plurality of expandable balloons and the proximal part serves as a handle. The shaft is preferably rigid, but need not be straight, so long as the positions of the expandable balloons are fixed and known. In the case of a flexible shaft, a semi-rigid molding device can be used to "save" the shape of the shaft after insertion, such that the positions of the expandable balloons can be determined. The shaft may be constructed of rigid, semi-rigid and flexible materials including, but not limited to, stainless steel, plastics and polyurethane.

Figure 6:
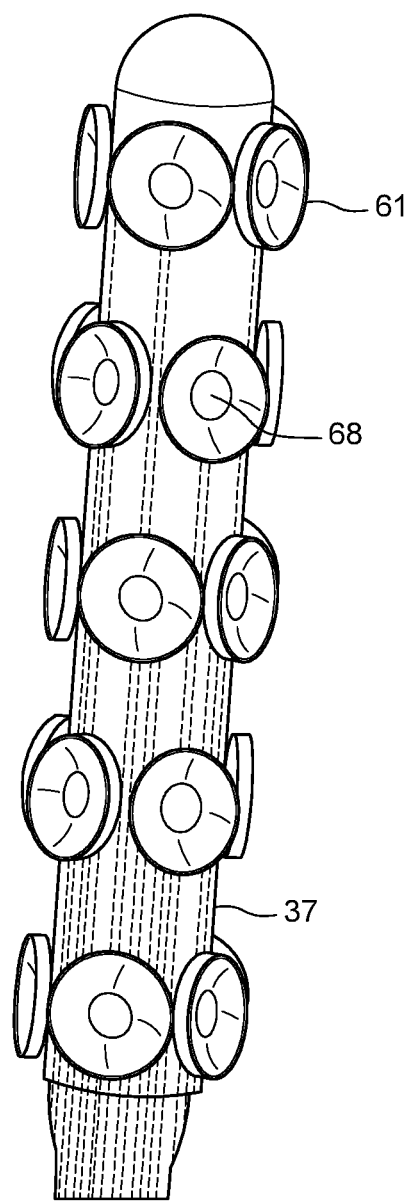
FIG. 6 shows a shaft with support structures.
Figure 7:
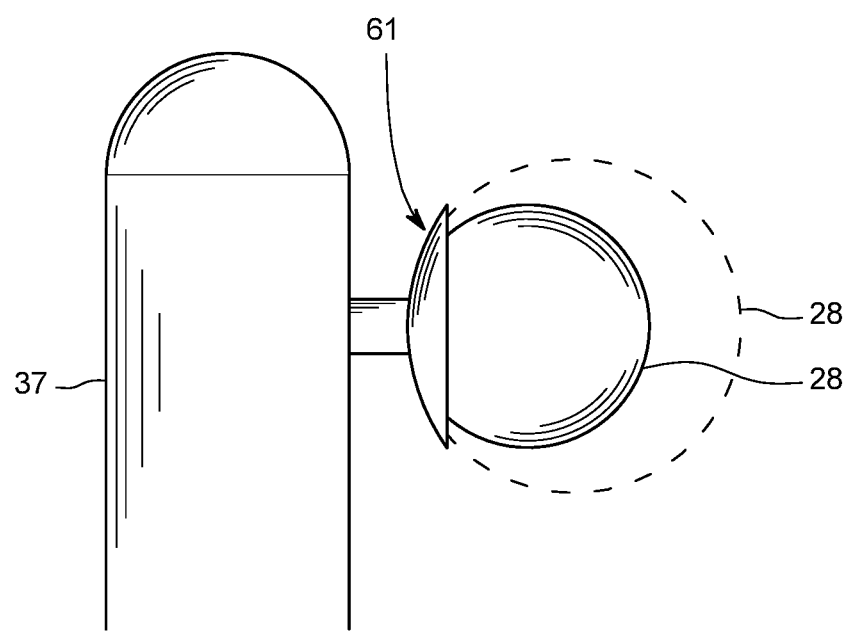
FIG. 7 shows a close-up side view of a balloon and support structure.

In the preferred embodiment, each expandable balloon is removably attached to the shaft at support cups such as 61. As shown in FIG. 7, support cup 61 is a segment of a sphere, such that the radius of the expanded balloon 28 does not exceed the radius of the support cup. This causes the spherical balloon to expand in alignment with the support cup, reducing shifting that might alter the position of the balloon. The uniform expansion of the balloon coupled with its known position are assumptions upon which the pessary model is based. FIG. 6 shows shaft 37 and support cups such as 61 without attached expandable balloons.

There can be any number of expandable balloons, as long as the position of each expandable balloon is fixed and known, and each balloon expands uniformly without losing its shape, which in the preferred embodiment is spherical. The balloons are preferably constructed with an elastomeric polymer but any flexible material may be used. Corresponding shaft openings such as 68 (see FIG. 6) are spaced such that the balloons do not overlap when expanding, which may cause them to abut against each other and deform their spherical shapes. In the preferred embodiment, each expandable balloon ranges from 15 to 30 mm in diameter, the shaft is 20 to 25 mm, such that the diameter of the device ranges from 55 to 85 mm in conformity with average pessary sizes today.

Figure 9:
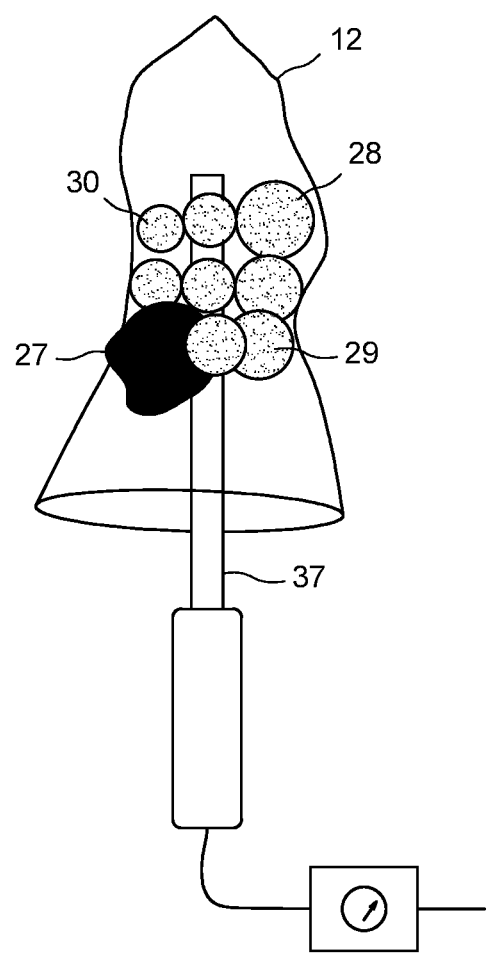
FIG. 9 shows an embodiment of the device with a urethral support balloon.

Insofar as the expandable balloons collectively form a balloon matrix that models the vaginal interior, it follows that the more expandable balloons there are in the matrix, the more "refined" the model. The expandable balloons may be arranged in any configuration as long as their positions are fixed. One or more balloons may not be spherical, so long as the one or more non-spherical balloons expand uniformly such that its dimensions can be correlated to its volume. For instance, as shown in FIG. 9, a "saddle" shaped urethral support balloon 27 abutting the bladder neck may be desired to model a pessary with a urethral support section for supporting the bladder neck, for the treatment of stress incontinence.

Figure 2:
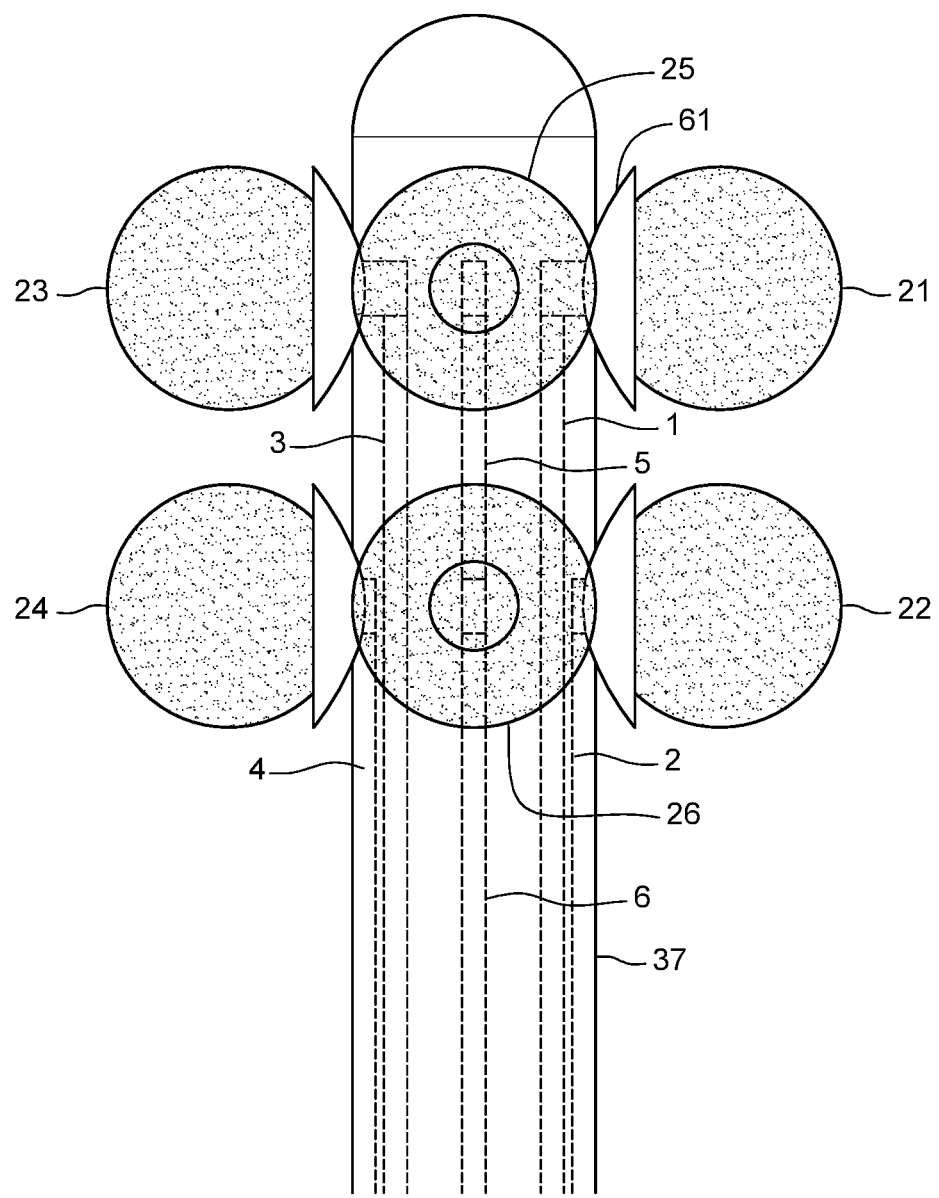
FIG. 2 shows a close-up, cross-section of the distal end of an embodiment of the device.

Each fill line delivers and extracts fluid to an expandable balloon corresponding to said fill line. In FIG. 2, fill line 1 delivers and extracts fluid to and from balloon 21, fill line 2 delivers and extracts fluid to and from balloon 22, and so on. A fill line may be any compatible fluid (liquid or gas) delivery line, including but not limited to tubes, pipes, ducts, and walls. Each fill line is connected at one end to an expandable balloon and at the other end to a fluid source that causes fluid to enter said expandable balloon.

Figure 3:
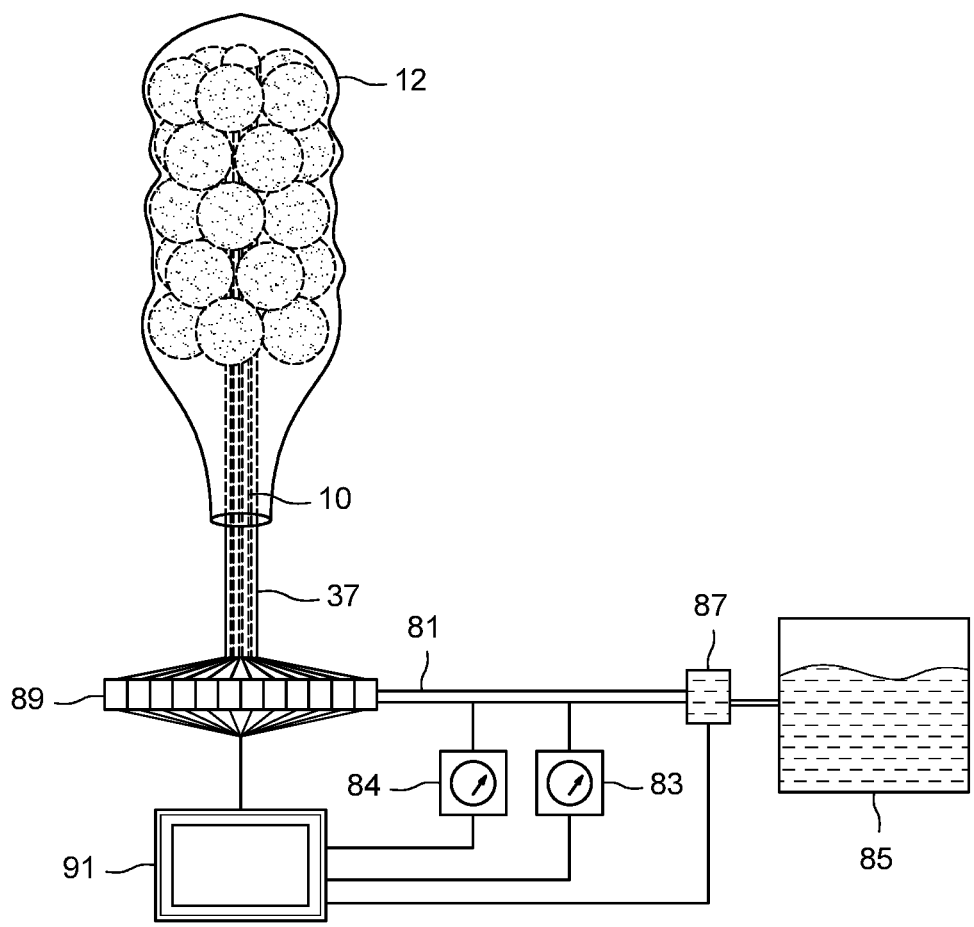
FIG. 3 shows a schematic overview of an embodiment of the system of the device.
Figure 8:
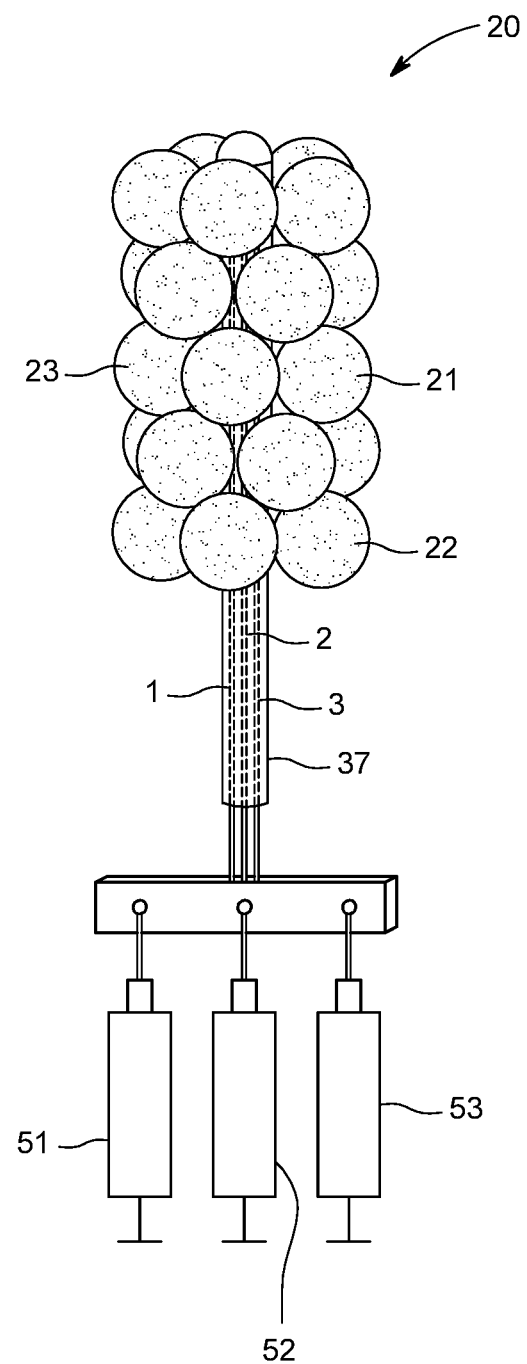
FIG. 8 shows a schematic overview of an embodiment of the system of the device.

In the simplest example, a fluid source can be a syringe. For instance, FIG. 8 shows fill lines 1, 2 and 3 connected to syringes 51, 52 and 53, respectively. In the preferred embodiment, the fluid source is an electromechanical valve such as a solenoid valve. FIG. 3 shows a solenoid valve manifold 89, in which each valve is connected to a fill line. The preferred embodiment facilitates control by a microcontroller 91. In that embodiment, the microcontroller 91 is also connected to send and receive data to/from reversible fluid pump 87, volumetric flowmeter 83 and optionally pressure gauge 84. Reversible fluid pump 87 transfers fluid between fluid reservoir 85 and the fill line via master line 81, which feeds valve manifold 89. Master line 81 may be of any size and length and the schematic depicted in FIG. 3 serves only to show connections between elements and not relative distances. In the preferred embodiment, reversible fluid pump 87 is a peristaltic pump but the invention may use any reversible fluid pump known in the art. The pump may be subject to manual or electronic control. If subject to electronic control, as shown in FIG. 3, reversible fluid pump 87 is coupled to microcontroller 91.

Fluid reservoir 85 receives, stores and is the source of fluid that can be delivered to each expandable balloon. The fluid reservoir is any reservoir including, but not limited to, tanks, drums, bags, etc. . . . . The fluid delivery system may comprise more than one fluid reservoir. For instance, each fill line could be served by a single reservoir and fluid pump for transferring fluid between the reservoir and the fill line.

The fill volume of each individual balloon is measured. In the preferred embodiment depicted in FIG. 3, the fill volume of each balloon is measured by a volumetric flowmeter 83 coupled to the delivery line 81. An alternative to the flowmeter is a visual volume marking on or in the reservoir. For instance, volume lines may be printed on the reservoir or a window of the reservoir to allow a clinician or user to take a visual measurement of the change in fill volume of each balloon as it is adjusted. It follows that the means for determining the fill volume of each balloon depends on the design of the fluid delivery system of the particular embodiment. For instance, in the simple example in which a syringe is the fluid source, volume markings on the syringe are the means for determining the fill volume. In another embodiment, markings on an expandable balloon may be a means to determine the fill volume of said balloon.

In the preferred embodiment, the invention further comprises a pressure gauge 84 for monitoring pressure in each balloon. Pressure data enables the clinician to refine the balloon volumes, by monitoring pressure exerted by corresponding balloon volumes that adequately support the vaginal walls without causing patient discomfort. Subjective input from the patient can help determine comfortable fit, and additional applied pressure at particular areas of the vaginal wall may be desirable for therapeutic purposes. For instance, additional pressure around the bladder neck may be desirable to treat urinary incontinence. Where gas is used, a temperature probe is attached to the distal part of the shaft, such that the volume of each balloon can be determined with reference to the ideal gas law.

The invention therefore is also a process for modeling a pessary, as follows: a modeling device comprised of a plurality of expandable balloons at fixed positions on a shaft is inserted into the vagina. The balloons, concurrently or consecutively, are expanded to a minimal volume such that little to no pressure is required. Then, each of the expandable balloons can be adjustably inflated and deflated to a desired pressure by operating a fluid delivery system to deliver fluid from a fluid source to said expandable balloon via a fill line. The fill volume of at least one of the expandable balloons is then applied to determine at least one dimension of at least one section of a pessary model.

Figure 4B:
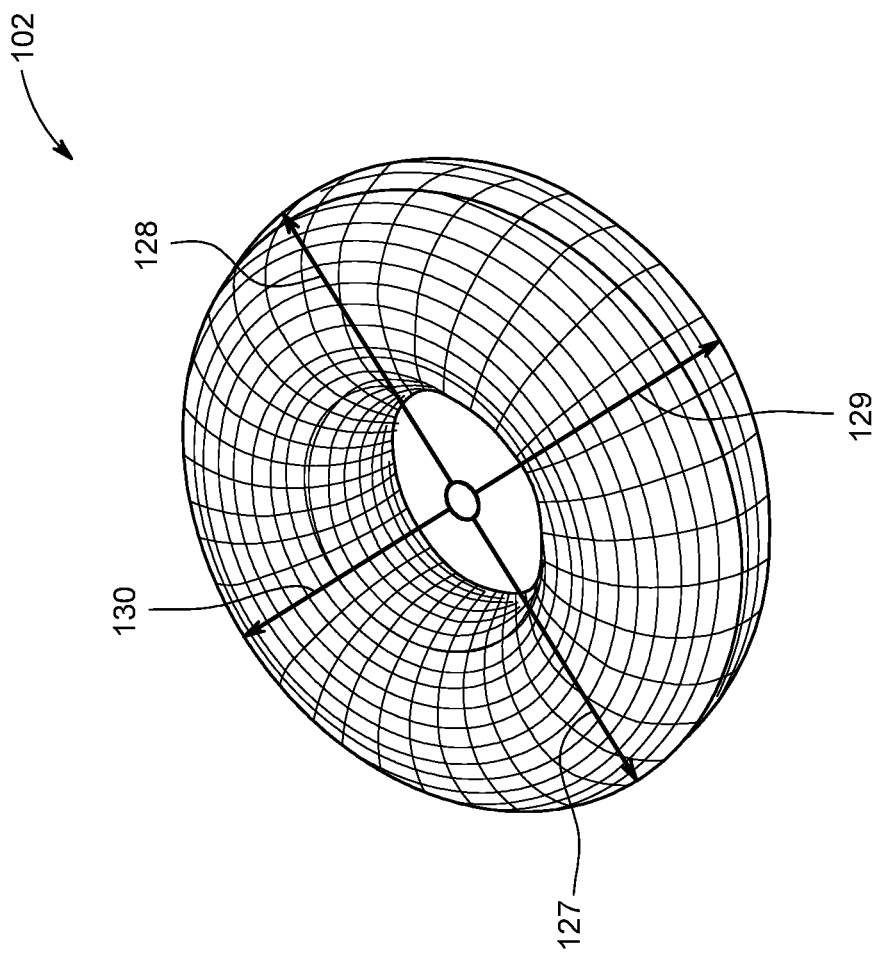
FIGS. 4A and 4B show how the device may be used to model a pessary with an existing computational model.
Figure 4A:
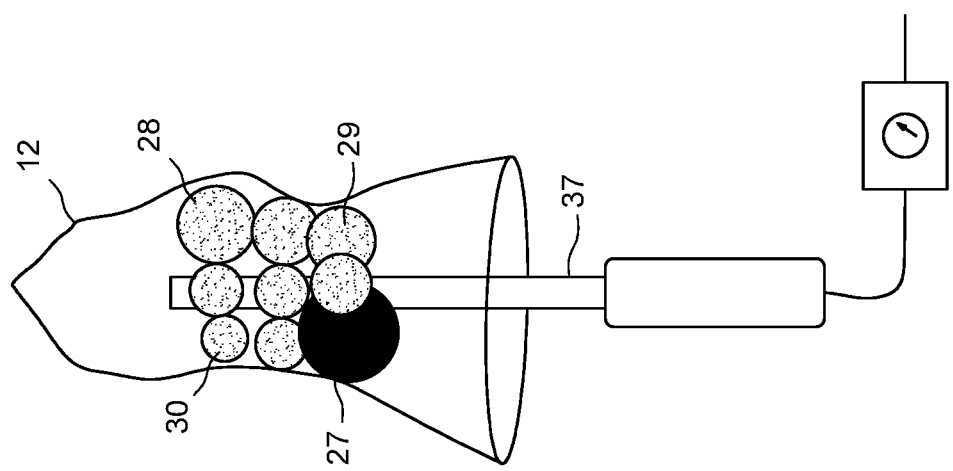

For example, as shown in FIGS. 4A and 4B, radial dimensions 127, 128, 129 and 130 of modeled ring pessary 102 can be determined with reference to the fill volume of balloons 27, 28, 29 and 30, respectively. In the simplest example, said at least one dimension can be input into an existing CAD model such as existing base case ring pessary 102. The resulting personalized model can be converted into any file format, such as STEP or STL, for manufacturing or 3D printing. In another sample implementation, the outside diameter of ring pessary 102 can be determined by the positions of balloons 27 and 28. Thus, the location of balloon "landmarks" and their diameter may be applied to determine the dimensions of the pessary.

Figure 5:
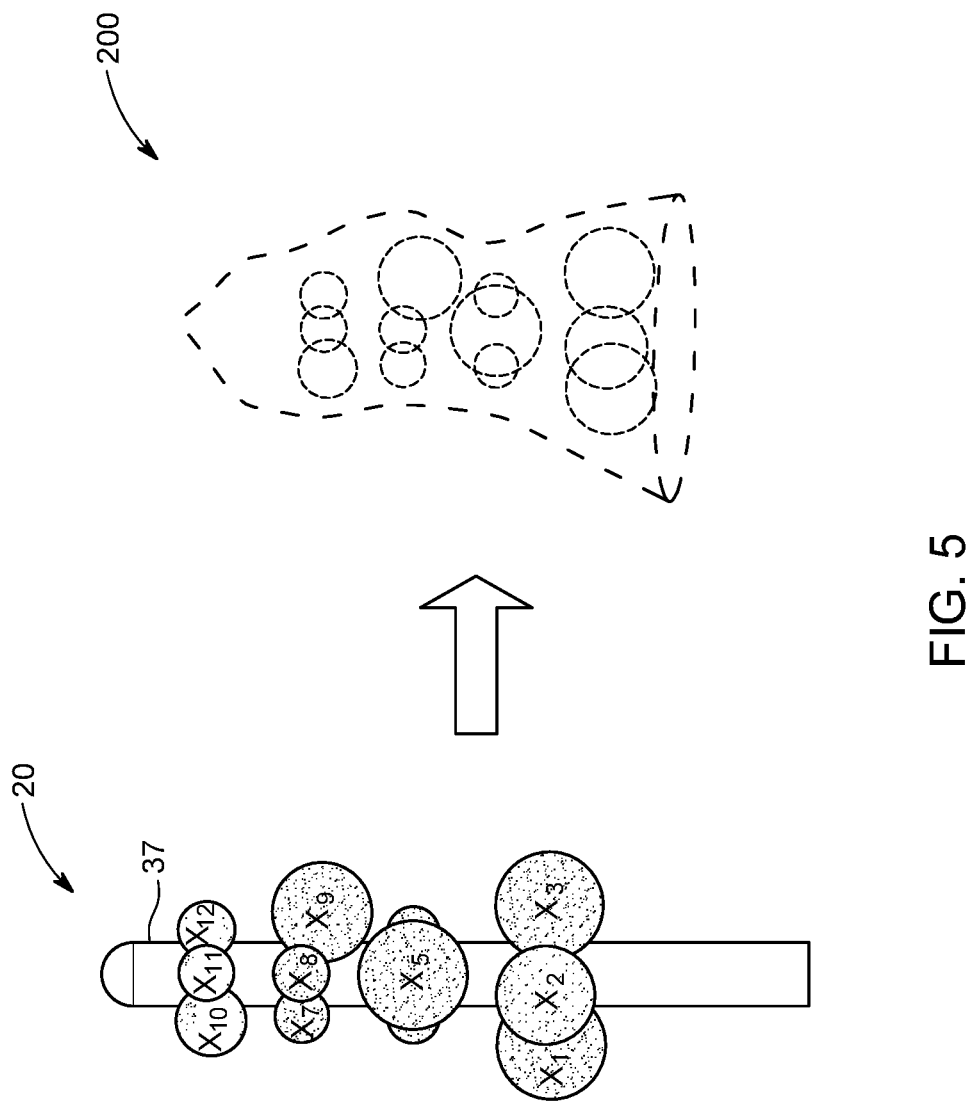
FIG. 5 shows an example of a full vaginal interior model based on the balloon matrix of the device.

A more generalized explanation of this step is as follows: the volume of each balloon of the plurality of balloons comprises a dataset $X=\{x_1, x_2, x_3, \ldots x_K\}$, such as the dataset $\{x_1, x_2, x_3, \ldots x_{12}\}$ corresponding to the labeled balloons in FIG. 5. This dataset is entered into a function that outputs a pessary model, which is essentially a set of rules for making a customized pessary. The size of the dataset may range from the fill volume for a single balloon, to the fill volume for each balloon of the balloon matrix. For instance, FIGS. 4A and 4B depict an example in which a ring pessary is determined by the data of four balloons, whereas FIG. 9 depicts an example in which a ring pessary with a "saddle" shaped urethral support 127 may even be determined by the volume of a single balloon 27. Insofar as the entire balloon matrix may be used to model the entire vaginal cavity, FIG. 5 shows how the volume for each balloon of the balloon matrix fully determines a model of that balloon matrix. A model corresponding to the entire balloon matrix may be desirable where computer aided design software is used to select different shapes, views, cuts, etc. . . . from the model. This type of model may also allow the clinician to experiment with new pessary designs and shapes.

In an alternative embodiment, the fill volume of each expandable balloon is recorded, and then the plurality of expandable balloons is removed from the vagina and reinflated outside of the vagina to the recorded fill volumes, whereby a physical model is created. In some cases or patients, the balloon matrix may even be removed from the vagina without need for deflation. The physical model is then used to create a pessary model. For instance, the physical model may be scanned and the resulting computational model used for further manipulation and/or manufacturing of the pessary shape. In another example, a mold may be taken of all or a part of the physical model, whereby the mold is used to manufacture customized pessaries.

The invention further comprises a removable sheath 12 that covers the balloon matrix. The sheath is sterile and biocompatible, and in the preferred embodiment, disposable, such that a new sheath is used and discarded each time the device is inserted into the patient. The sheath is preferably constructed of polyurethane or nitrile, but can be constructed of any hypoallergenic flexible material. The sheath facilitates insertion and removal, and can also carry lubricant.

In another embodiment of the invention, the sheath functions as part of the modeling mechanism of the device. In particular, the sheath may have additional functionalities when the balloon fill amounts are determined by optical scanning or other image scanning techniques. For instance, the sheath naturally performs smoothing functions that may refine a computer-aided design model, or its surface may prints and/or coatings that facilitate data collection by optical scanner. Furthermore, prints and/or coatings on the inside of the sheath may facilitate the use of an endoscopic camera that is inserted into the vagina or the shaft of the device for additional data collection from the interior. Other imaging solutions, such as CT scan and MRI, typically require contrast material, which can be deposited directly on the sheath.

In yet another embodiment, the sheath comprises two layers such that it can be used for molding by the injection of a hardenable material. For instance, following customized inflation of the balloon matrix, a curable polymer is injected between two layers of the sheath and cured. The inner layer is translucent and the outer layer is protective, such that UV-light can be shined into the cavity to stiffen the polymer into a semi-rigid shape, without harm to surrounding tissue. The device can then be removed from the body and the sheath discarded. The result is a physical model of the internal geometry of the wall of the cavity.

The invention claimed is:

1. A device for modeling a pessary, comprising:
    a matrix of expandable balloons that are substantially spherical and attachable to an outer surface of a hollow shaft at fixed openings on the outer surface, the matrix having at least two rows wherein each row is a circumferential ring around the outer surface of the shaft, the hollow shaft housing fill lines serving each fixed opening, such that the shaft supports the matrix of expandable balloons for vaginal insertion, and wherein each expandable balloon of the matrix of expandable balloons is coupled to a fill line for transferring fluid to the expandable balloon;
    a fluid source for each said fill line;
    a means for measuring a fill volume for each expandable balloon, wherein the means for measuring the fill volume for each expandable balloon is a flowmeter coupled to the fluid source.

2. The device of claim 1 wherein the fluid source is a fluid delivery system comprised of:
    a valve;
    a fluid reservoir, whereby the fluid reservoir is the source of fluid for delivery to the matrix of expandable balloons; and
    a reversible fluid pump, whereby the reversible fluid pump transfers fluid between the fluid reservoir and the fill line.

3. The device of claim 2 wherein the fluid delivery system further comprises a solenoid valve manifold and a microcontroller for selecting the valve.

4. The device of claim 1 further comprising a sheath for covering the matrix of expandable balloons, wherein the sheath is physiologically compatible and disposable.

5. The device of claim 4 wherein the sheath comprises two layers whereby a curable polymer can be received in between the two layers.

6. The device of claim 1 wherein each expandable balloon of the matrix of expandable balloons nests in a corresponding support cup on the shaft, the support cup comprising a segment of a sphere having a support cup radius, whereby the expandable balloon has a radius that shall not exceed the support cup radius.

7. The device of claim 1 wherein the matrix of expandable balloons comprises at least one non-spherical urethral support balloon.

8. The device of claim 1 wherein the fluid source is a syringe.

9. The device of claim 1 wherein the means for measuring the fill volume for each expandable balloon is a volume marking on the fluid source.

10. A process for modeling a pessary comprising the steps of:
    (i) inserting into a vagina a modeling device comprised of a matrix of expandable balloons that are substantially spherical and attachable to an outer surface of a hollow shaft at fixed openings on the outer surface, the matrix having at least two rows wherein each row is a circumferential ring around the outer surface of the shaft, the hollow shaft housing fill lines serving each fixed opening, such that the shaft supports the matrix of expandable balloons for vaginal insertion, and wherein each expandable balloon of the matrix of expandable balloons is coupled to a fill line for transferring fluid to the expandable balloon;

(ii) inflating each expandable balloon to a size by operating a fluid source that causes fluid to enter the fill line and thereby transfer fluid to the expandable balloon corresponding to said fill line;

(iii) measuring a fill volume for at least one expandable balloon; and (iv) applying the fill volume for each expandable balloon to determine at least one dimension of at least one section of a pessary model.

11. The process of claim 10 wherein the pessary model is a ring pessary model having a urethral support element, wherein a length and width of the urethral support element section is determined.

12. The process of claim 10 wherein the pessary model is a ring pessary model having an outside diameter, and the at least one dimension of the at least one section of the pessary model is the outside diameter.

13. The process of claim 10 wherein the fill volume for the at least one balloon is measured using a flowmeter.

14. The process of claim 10 wherein the fill volume for the at least one balloon is measured by reading a volume marking on the fluid source.

15. A process for modeling a pessary comprising the steps of:

(i) inserting into a vagina a modeling device comprised of a matrix of expandable balloons that are substantially spherical and attachable to the outer surface of a hollow shaft at fixed openings on the outer surface, the matrix having at least two rows wherein each row is a circumferential ring around the outer surface of the shaft, the hollow shaft housing fill lines serving each fixed opening, such that the shaft supports the matrix of expandable balloons for vaginal insertion, and wherein each expandable balloon of the matrix of expandable balloons is coupled to a fill line for transferring fluid to the expandable balloon;

(ii) inflating each expandable balloon to a size by operating a fluid source that causes fluid to enter the fill line and thereby transfer fluid to the expandable balloon corresponding to said fill line;

(iii) measuring the fill volume of each expandable balloon; and (iv) removing the modeling device from the vagina.

16. The process of claim 15 further comprising the step of optically scanning the modeling device.

17. The process of claim 15 wherein the fill volume of each expandable balloon is measured using a flowmeter.

18. The process of claim 15 wherein the fill volume of each expandable balloon is measured using a volume marking on the fluid source.

19. A device for mapping a vaginal canal, the device comprising:

a shaft for defining a plurality of confined flow passageways;

an array of expandable balloons mounted around the shaft, the array having at least two rows of circumferential rings around the shaft; and a fluid source for expanding each said expandable balloon, each expandable balloon being in communication with said fluid source through one of said confined flow passageways.

20. The device of claim 19 wherein the array of expandable balloons further comprises at least one non-spherical urethral support balloon.

\* \* \* \* \*